(12) United States Patent
Some (10) Patent No.: US 7,365,836 B2
(45) Date of Patent: Apr. 29, 2008

(54) HIGH SPEED LASER SCANNING INSPECTION SYSTEM

(75) Inventor: Daniel Some, Ashdod (IL)

(73) Assignee: Applied Materials, Israel, Ltd., Rehovot (IL)

( * ) Notice: Subject to any disclaimer, the term of this patent is extended or adjusted under 35 U.S.C. 154(b) by 126 days.

(21) Appl. No.: 11/317,156

(22) Filed: Dec. 22, 2005

(65) Prior Publication Data

US 2006/0132758 A1 Jun. 22, 2006

Related U.S. Application Data

(62) Division of application No. 10/386,973, filed on Mar. 11, 2003.

(60) Provisional application No. 60/378,721, filed on May 7, 2002, provisional application No. 60/378,400, filed on May 6, 2002.

(51) Int. Cl.
*G01N 21/00* (2006.01)

(52) U.S. Cl. ............................ 356/237.4; 356/237.2; 356/237.5

(58) Field of Classification Search ............. None
See application file for complete search history.

(56) References Cited

U.S. PATENT DOCUMENTS

| 5,461,474 A | * | 10/1995 | Yoshii et al. ............ 356/237.4 |
| 6,018,413 A | * | 1/2000 | Oka ......................... 359/326 |
| 6,621,571 B1 | * | 9/2003 | Maeda et al. ........... 356/237.5 |
| 6,636,301 B1 | * | 10/2003 | Kvamme et al. ........ 356/237.2 |
| 6,809,808 B2 | * | 10/2004 | Feldman et al. ......... 356/237.1 |
| 6,879,390 B1 | * | 4/2005 | Kvamme et al. ........ 356/237.2 |
| 2004/0042001 A1 | * | 3/2004 | Vaez-Iravani et al. ... 356/237.2 |

* cited by examiner

*Primary Examiner*—Gregory J. Toatley, Jr.
*Assistant Examiner*—Juan D Valentin, II
(74) *Attorney, Agent, or Firm*—Tarek N Fahmi (57) ABSTRACT

An optical inspection system rapidly evaluates a substrate by illumination of an area of a substrate larger than a diffraction-limited spot using a coherent laser beam by breaking temporal or spatial coherence. Picosecond or femtosecond pulses from a modelocked laser source are split into a plurality of spatially separated beamlets that are temporally and/or frequency dispersed, and then focused onto a plurality of spots on the substrate. Adjacent spots, which can overlap by up to about 60-70 percent, are illuminated at different times, or at different frequencies, and do not produce mutually interfering coherence effects. Bright-field and dark-field detection schemes are used in various combinations in different embodiments of the system.

4 Claims, 7 Drawing Sheets

FIG. 12

HIGH SPEED LASER SCANNING INSPECTION SYSTEM

CROSS REFERENCES TO RELATED APPLICATIONS

The present patent application is a divisional application of U.S. application Ser. No. 10/386,973 filed Mar. 11, 2003, and is herein incorporated by reference.

This application claims the benefit of U.S. provisional patent application No. 60/378,400 filed 6 May 2002 titled "High speed laser inspection system" and claims the benefit of U.S. provisional patent application No. 60/378,721 filed 7 May 2002 titled "Optical technique for detecting buried defects in opaque films".

BACKGROUND OF THE INVENTION

1. Field of the Invention

This invention relates generally to systems and methods for detecting irregularities on a substrate. More particularly, this invention relates to systems and methods for detecting irregularities on the surface of silicon wafers or photomasks.

2. Description of the Related Art

Semiconductor wafers are inspected prior to, during, and after patterning procedures. Optical inspection systems typically employ illumination optics and collection-detection optics for directing incident light from a light source onto a wafer to be inspected, and observing returned light.

Imaging techniques are often employed in modern inspection systems. These systems are classified according to the direction of the illumination with respect to the collection optics. If the illumination impinges upon the substrate from a direction such that the transmitted or specularly reflected light is collected by the imaging optics, the system is termed "bright field" (BF). If, on the other hand, the transmitted or specularly reflected light arrives from a direction, which is outside the collection angle of the collection optics, the system is termed "dark field" (DF).

Today, semiconductor wafers are inspected using bright-field techniques, dark-field techniques, or combinations thereof. Coherent light is commonly employed for illumination.

Lasers, which are commonly used in inspection systems produce undesirable coherent phenomena in imaging systems, such as ringing of edges and speckles. Schemes exist for destroying the coherence of laser sources, but they inevitably add to the system's complexity and reduce optical power. Laser-scanning inspection systems typically employ a focused laser spot scanning over the sample. The reflected or scattered light is collected by a detector, which may be non-imaging, e.g., a photomultiplier tube, partially imaging, e.g., a linear CCD, or fully imaging, e.g., an area CCD. Each of these entails certain advantages and limitations.

With a non-imaging detector, the system resolution is determined solely by the illuminated area, as all the collected light is integrated into a single signal. This scheme precludes multi-spot, line and area illumination schemes. Throughput is limited by the spot size and the scan rate. Usually the beam is scanned over the sample using a rotating polygon mirror, acousto-optic device scanner, or oscillating galvanometric scanning mirror.

With a partially imaging or fully imaging detector, light is collected simultaneously from a larger region of the sample so that multiple spots may be illuminated simultaneously, multiplying the previous throughput by the number of illumination spots. However, if these spots are not spatially separated, image distortions may occur due to coherent interference effects.

It may be advantageous to simultaneously collect both the reflected or bright-field image, at high spatial resolution at high throughput, and the scattered or dark-field image, at lower spatial resolution at low throughput. The advantage is related to the difference in throughput achievable with optimal detectors for the bright-field image (partially imaging or fully imaging), as compared with the dark-field (non-imaging). One method for achieving simultaneous bright- and dark-field detection is addressed in commonly assigned U.S. Pat. No. 6,122,046 to Almogy, the disclosure of which is herein incorporated by reference, wherein a large spot on a substrate is illuminated using optics having a low numerical aperture (NA). Dark-field detection is achieved by a non-imaging detector. The dark-field resolution is determined by the illumination spot size. The bright-field signal is collected with high NA optics, and imaged onto an area detector, providing improved resolution relative to the dark field detector by a factor that is the ratio of the collection NA to the illumination NA. However, when using imagine detectors, the bright-field images may suffer undesirable distortion due to coherence effects in the form of ringing at feature edges, if there is mismatch between the NA of the collection optics and the imaging optics. When detection is performed with non-imaging detectors, which generally have lower resolution than imaging detectors, these coherence effects can usually be disregarded.

SUMMARY OF THE INVENTION

The invention provides an apparatus and method for rapidly inspecting a substrate by illuminating an area of a substrate that is larger than a diffraction-limited spot without undesirable interference effects.

The invention provides an apparatus and method for illuminating a large area of a substrate using high-NA imaging optics and using imaging detectors without incurring undesirable coherence interference effects.

The invention provides an apparatus and method for breaking temporal or spatial coherence of a pulsed beam of coherent light. In some embodiments of the present invention, ultrafast scanning is achieved using picosecond or femtosecond pulses from a modelocked laser source. The pulsed laser beam is split into a plurality of beamlets, each of which follows a path having a uniquely different length. The beamlets are respectively focused onto a plurality of spots. Adjacent spots are illuminated at different times, and therefore do not mutually interfere.

Other embodiments of the invention exploit the large spectral bandwidth produced by laser pulses, which are femtoseconds or picoseconds in duration. In some of these embodiments, beamlets having different frequencies are dispersed temporally. In other embodiments, the beamlets having different frequencies are dispersed spatially. In any case, the dispersion illuminates different spots on the substrate, without interference.

In the above-noted embodiments, high-resolution detection may be performed with an imaging detector. Additionally or alternatively, one or more single-element detectors having a high NA may be employed. In those embodiments employing frequency dispersion, different single element detectors can be sensitive to different frequencies. Optionally, dark-field detectors can be additionally provided. Typically non-imaging dark-field detectors have a high NA, and operate by simultaneously collecting the light scattered from all illuminated spots. The spots are usually orthogonal or somewhat oblique to a primary scan direction. The NA of an imaging dark-field detector is typically matched to the illumination spot size.

The invention provides an apparatus for optical inspection, including a coherent light source for producing a pulsed beam, and a beam converter or manipulator for dividing the beam into a plurality of spatially separated beamlets that are incident on a substrate to be inspected. Each of the beamlets illuminates a different spot on the substrate, such that responsively to the beam converter, there is substantially no mutual interference between the beamlets that illuminate adjacent spots. The apparatus includes a scanner for displacing the beamlets across the substrate, and a detector, which is disposed in a path of light of the beamlets that is reflected from the substrate.

According to one aspect of the apparatus, the centers of at least two of the different spots are spaced apart by no more than about 3 spot diameters. Different spots may be in mutual contact, and may overlap by up to about 60-70 percent.

According to one aspect of the apparatus, the light source is a modelocked laser.

According to another aspect of the apparatus, the scanner includes a first scanner for displacing the beamlets in a primary scanning direction and a second scanner for displacing the beamlets in a secondary scanning direction.

According to a further aspect of the apparatus, the detector is a bright-field detector.

According to yet another aspect of the apparatus, the detector also includes a dark-field detector.

According to still another aspect of the apparatus, the detector is a single-element detector.

According to an additional aspect of the apparatus, the detector includes a plurality of single-element detectors.

According to another aspect of the apparatus, each of the single-element detectors is sensitive to a different waveband.

According to one aspect of the apparatus, the detector is an imaging detector.

According to still another aspect of the apparatus, the detector is an imaging detector in a first scanning direction and a non-imaging detector in a second scanning direction.

According to a further aspect of the apparatus, the beamlets are incident normally to the substrate.

According to yet another aspect of the apparatus, the beamlets are incident obliquely to the substrate.

According to one aspect of the apparatus, the beam converter includes a wavelength beam converter.

According to another aspect of the apparatus, the beam converter includes a temporal beam converter.

According to yet another aspect of the apparatus, the temporal beam converter includes a plurality of beamsplitters and a plurality of retroreflectors, wherein a light path of each of the beamlets extends through at least one of the beamsplitters and through one of the retroreflectors.

According to yet another aspect of the apparatus, the temporal beam converter includes a plurality of optical fibers has different lengths, wherein a light path of each of the beamlets extends through a corresponding one of the fibers.

According to still another aspect of the apparatus, the temporal beam converter includes a plurality of edge filters and a plurality of retroreflectors, wherein a light path of each of the beamlets extends through at least one of the edge filters and through one of the retroreflectors.

The invention provides a method of optical inspection, which is carried out by emitting a pulsed beam of coherent light, dispersing the beam into a plurality of spatially separated beamlets, and impinging the beamlets onto a substrate to be inspected, wherein each of the beamlets illuminates a different spot on the substrate and there is substantially no mutual interference between the beamlets that illuminate adjacent spots on the substrate. The method is further carried out by displacing the beamlets across the substrate, and detecting reflections of the beamlets from the substrate.

According to one aspect of the method, the centers of at least two of the different spots are spaced apart by no more than about 3 spot diameters. Different spots may be in mutual contact, and may overlap by up to about 60-70 percent.

In a further aspect of the method converting is performed by temporal dispersion.

In yet another aspect of the method converting is performed by wavelength dispersion.

In an additional aspect of the method the beamlets are displaced in a primary scanning direction and in a secondary scanning direction.

In still another aspect of the method scattered light of the beamlets from the substrate is detected.

Yet another aspect of the method detecting is performed using a single-element detector.

A further aspect of the method detecting is performed using a plurality of single-element detectors.

According to another aspect of the method, each of the single-element detectors is sensitive to a different waveband.

In one aspect of the method detecting is performed using an imaging detector.

In an additional aspect of the method detecting is performed using an imaging detector in a first scanning direction and a non-imaging detector in a second scanning direction.

According to an additional aspect of the method, the beamlets are impinged normally to the substrate.

According to still another aspect of the method, the beamlets are impinged obliquely to the substrate.

According to an additional aspect of the method converting is performed by imposing a frequency chirp on pulses of the beam.

The invention provides an apparatus for optical inspection, including a coherent light source for producing a pulsed beam, and a wavelength beam converter for dividing the beam into a plurality of spatially separated beamlets that are incident on a substrate to be inspected. Each of the beamlets has a different waveband and illuminates a different spot on the substrate. The apparatus includes a scanner for displacing the beamlets across the substrate, and a detector disposed in a path of reflected light from the substrate of the beamlets.

BRIEF DESCRIPTION OF THE DRAWINGS

For a better understanding of these and other objects of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances well-known circuits, and control logic have not been shown in detail in order not to unnecessarily obscure the present invention.

Notation.

The following notation is used herein:

$c$ is the speed of light in a relevant medium;

R is the scan rate in pixels/second along a primary scan direction;

r is the scan rate in pixels/second along a secondary scan direction, transverse to the primary scan direction;

T is the time between successive pulses emitted from a modelocked laser; and $\tau$ is the duration in time of a pulse emitted from the modelocked laser.

Overview.

Figure 1:
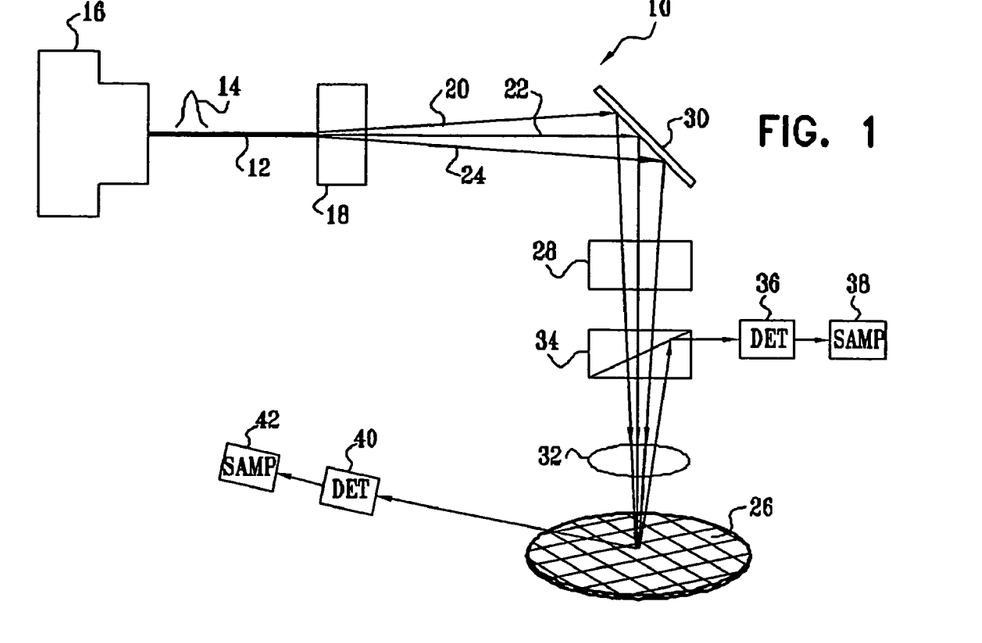
FIG. 1 is a high level schematic illustration of an optical inspection system, which is constructed and operative in accordance with a disclosed embodiment of the invention.

Turning now to the drawings, reference is initially made to FIG. 1, which is a high level schematic illustration of an optical inspection system 10 that is constructed and operative in accordance with a disclosed embodiment of the invention. Using the system 10, ultrafast scanning is achieved using a pulsed beam 12 of coherent light, shown representatively as a pulse 14. The pulse 14 may typically vary in duration from a few picoseconds to femtoseconds, and is emitted from a modelocked laser source 16. Alternatively, longer or shorter pulse durations may be used in some applications.

Suitable values for the pulse interval T of the beam 12 are 1-20 nsec, In the embodiments disclosed below utilizing temporal dispersion, but not spectral dispersion, pulse durations of 10-100 psec are suitable for the pulse 14. In embodiments that employ spectral separation, pulse durations $\tau$ from 100 fsec-10 psec are suitable.

For embodiments in which femtosecond pulses are generated, the model Vitesse 800, available from Coherent Inc., 5100 Patrick Henry Drive, Santa Clara, Calif. 95054 USA, is suitable for the laser source 16. The model Vitesse 8000 produces pulses having an 8 nm bandwidth, which allows for temporal dispersal at a resolution of 10-20 beamlets per pulse interval, as is disclosed in further detail hereinbelow.

For embodiments in which picosecond pulses are generated, the laser source 16 can be the model IC-532-1000, manufactured by High-Q Laser Production GmbH, Kaiser-Franz-Josef-Str. 61, A-6845 Hohenems, Austria. The model IC-532-1000 operates with a pulse interval of 12.5 nsec and a pulse duration of 6 psec. Although the system 10 is capable of generating up to 1000 differently timed pulsed beamlets during each pulse interval of the laser source 16, each beamlet being separated from the next by twice the pulse duration, it is practical to operate the model IC-532-1000 in arrangements producing 10-20 individual beamlets per pulse interval.

The beam 12 enters a beam converter 18, which divides the beam 12 into a plurality of spatially separated beamlets 20, 22, 24. The beamlets 20, 22, 24 are displaced relative to a substrate 26 by a scanner 28, and are impinged on the substrate 26 by directing optics 30 and focusing optics 32, so that each beamlet illuminates a different spot. The beamlets 20, 22, 24 should optimally focus to diffraction-limited spots, which overlap by about 60-70% in order to generate a uniformly illuminated line.

In some embodiments the beamlets 20, 22, 24 are dispersed by the beam converter 18 according to wavelength. In other embodiments the beamlets 20, 22, 24 are dispersed temporally, so that pulses therein each occupy a unique time interval. In still other embodiments, both temporal and wavelength dispersion are produced in combination by the beam converter 18. Different embodiments of the beam converter 18 are disclosed in further detail hereinbelow.

The scanner 28, which can be any suitable optical deflection system, moves the beamlets 20, 22, 24 across the substrate 26 in a primary scanning direction. Movement in a secondary scanning direction, which is usually orthogonal to the primary scanning direction, is typically achieved by mechanical displacement of the substrate 26 relative to the focusing optics 32. This can be accomplished by a mechanical stage (not shown). In some embodiments, the scanner 28 can be a 2-dimensional scanner, in which case the mechanical stage can be omitted. Light within the specular angular range returns from the substrate 26 to beam processing optics 34 and is detected and processed by a bright-field detector 36 and a data sampler 38. The detector 36 can be an imaging detector, and should be CCD or CMOS-based. The number of detector elements is application dependent. A configuration of at least 2000×n pixels is typical, where n is the number of beamlets in the secondary scanning direction.

The detector 36 should be capable of transferring data at the rate (nR) pixels/sec. As used herein, the terms "primary scanning direction" and "secondary scanning direction" are used arbitrarily to distinguish scanning directions. These terms otherwise have no physical meanings with respect to the actual configuration of the system 10.

Optionally, a dark-field detector 40 and a data sampler 42 may be provided for light that is scattered by the substrate 26. The techniques disclosed in the above-noted U.S. Pat. No. 6,122,046 are suitable when both the detector 36 and the detector 40 are operated together. The detector 40 can be a non-imaging detector, such as the model R6355 photomultiplier tube, manufactured by Hamamatsu Photonics K.K., 314-5, Shimokanzo, Toyooka-village, Iwata-gun, Shizuoka-ken, 438-0193, Japan.

An imaging dark-field detector may be used as the detector 40. It can have a relatively low resolution, as there is a low signal-to-noise ratio. In such case, the NA of the collection optics should be matched to the total illumination on the substrate. A low NA is typically chosen, in order to spatially integrate over the secondary scanning direction, that is the linear area that is illuminated at any particular time during a continuous scanning operation.

Figure 2:
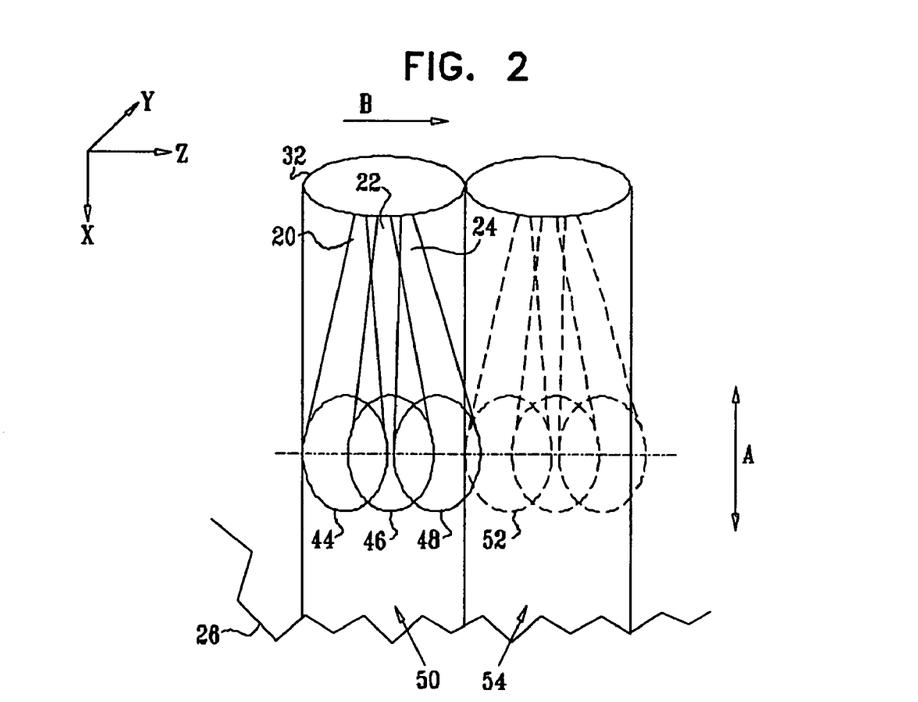
FIG. 2 is an enlarged schematic view of optics in the system shown in FIG. 1, illustrating illumination of a substrate in accordance with a disclosed embodiment of the invention.

Reference is now made to FIG. 2, which is an enlarged schematic view of optics in the system 10 (FIG. 1), illustrating illumination of the substrate 26 in further detail. The beamlets 20, 22, 24 illuminate spots 44, 46, 48 on the substrate 26. With reference to the coordinate system shown in FIG. 2, scanning motion in the primary direction along the X-axis is indicated by a double-headed arrow A, while scanning motion in the secondary direction along the Z-axis is shown by a single-headed arrow B. The individual spots 44, 46, 48 should partially overlap, as noted above, in order to produce both a uniform line section and to sample the substrate within the Nyquist frequency, as is well-known from sampling theory. The overlap should be about 60-70%. Below this range, performance progressively degrades. However, in some embodiments, using either temporal or spectral separation, some benefit of the system 10 will be seen, even when the centers of non-contiguous neighboring spots are spaced apart by up to 3 to 4 spot sizes or diameters.

In high-speed scanning applications, which are required in a production environment, movements in the primary and secondary scanning directions are coordinated such that there is an overlap of the about 60-70% between the spot illuminated by the last beamlet of one secondary scan, and the first beamlet of the next. This can be appreciated in FIG. 2, in which the last illuminated spot on a strip 50, that is the spot 48, overlaps a first spot 52 on an adjacent strip 54.

First Embodiment

Figure 3:
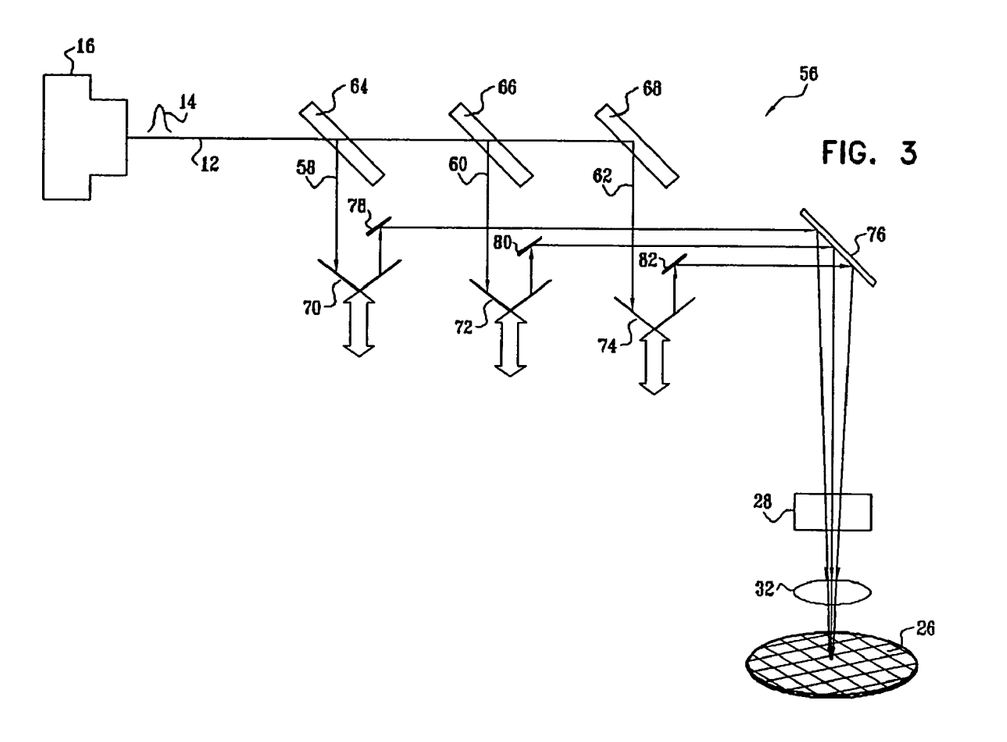
FIG. 3 is a schematic illustration of an optical inspection system employing multiple pulsed, temporally dispersed and spatially separated beamlets, which is constructed and operative in accordance with a disclosed embodiment of the invention.

Reference is now made to FIG. 3, which is a schematic illustration of an optical inspection system 56, which is constructed and operative in accordance with a disclosed embodiment of the invention.

The beam 12 is split into a plurality of beamlets 58, 60, 62 by beamsplitters 64, 66, 68, respectively. The relative reflectance and transmittance of each of the beamsplitters 64, 66, 68 are typically (but not necessarily) chosen so that all the beamlets 58, 60, 62 have equal intensities. The beamlets 58, 60, 62 are received respectively by retroreflectors 70, 72, 74. The beamlets 58, 60, 62 are then directed to a reflector 76 by reflectors 78, 80, 82, after which they pass through the scanner 28, beam processing optics 34 and focusing optics 32, and impinge on the substrate 26. The retroreflectors 70, 72, 74 form free-space delay lines. They are disposed so that the optical paths of the beamlets 58, 60, 62 are of different lengths. Thus, the beamsplitters 64, 66, 68 and the retroreflectors 70, 72, 74 cooperate to constitute a temporal manipulator for the beam 12.

The beamlets 58, 60, 62 are focused onto adjacent spots on the substrate 26, but since they arrive at different times, they do not mutually interfere. In some embodiments, the beamlets 58, 60, 62 are oblique to the substrate 26. In other embodiments the beamlets 58, 60, 62 are normal to the substrate 26. While it is possible to produce a series of beamlets, e.g., 20, each having a different time delay or wavelength, in practice it may be more convenient to generate only a few at a time, e.g., five, each having a different delay and/or waveband, the spots typically, but not necessarily, overlapping by about 60-70% to produce a short linear segment in which the beams have no mutual interference, This segment can be replicated 4 times in different locations to produce a line of illumination, on the substrate 26 equivalent to 20 beamlets. Beamlets in different segments having the same delays or wavebands are sufficiently spaced apart from one another to avoid mutual interference.

The path lengths of the beamlets 58, 60, 62 are set to differ by a factor of at least $2\tau/c$. For a 10 psec pulse, the path difference between adjacent spots is approximately 6 mm in vacuum, and approximately 4 mm in glass (refractive index=1.5). The total number of spots $n_{max}$ in the secondary scanning direction is limited to $n_{max}=T/2\tau$, where T is the time between successive pulses exiting the laser. The effective cross-scan rate for the actual number of spots n is r=n/T, and the effective total scan rate $R_{eff}$ increases to $R_{eff}=Rn$, as compared with the total scan rate R that is achieved when only one spot is illuminated.

Second Embodiment

Figure 4:
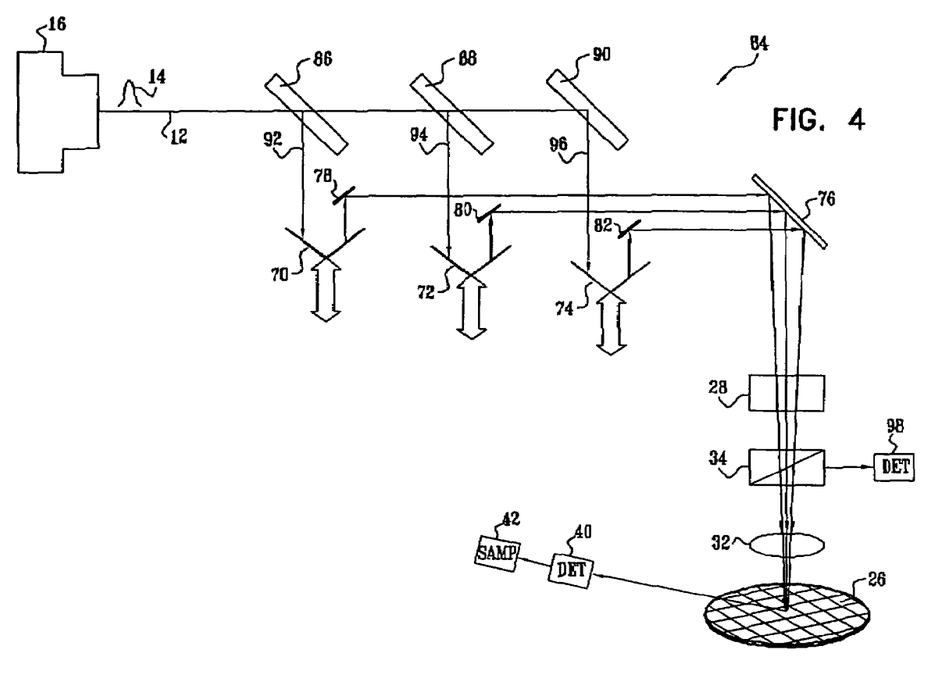
FIG. 4 is a schematic illustration of an optical inspection system employing multiple pulsed spatially separated beamlets, dispersed temporally and by waveband, which is constructed and operative in accordance with an alternate embodiment of the invention.

Reference is now made to FIG. 4, which is a schematic illustration of an optical inspection system 84, which is constructed and operative in accordance with an alternate embodiment of the invention. The description of FIG. 4 should be read in conjunction with FIG. 3. The arrangement of the system 84 is similar to the system 56, except now, the beamsplitters 64, 66, 68 (FIG. 3) are replaced by a series of reflective edge filters 86, 88, 90, which produce beamlets 92; 94, 96, each having a unique waveband.

The ultrafast pulse 14 inherently contains a large spectral bandwidth, with a minimum bandwidth $\Delta v$ given by: $\Delta v \cdot \tau \cong 1$. The beamlets 92, 94, 96 are spatially separated, and not only are dispersed temporally as disclosed in the discussion of the embodiment of FIG. 3, but are also distributed according to wavelength, using the edge filters 86, 88, 90, which disperse the beamlets 92, 94, 96 according to wavelength. For example, a typical 100 fsec pulse with a central wavelength of 800 nm has an operational spectral width of about 20 nm. In the system 84, a bright-field detector unit 98 may include a plurality of individual detectors, each sensitive to a particular waveband, or it may include one or more detectors with wideband sensitivity.

Dispersing the beam 12 into different wavelength components is sufficient to break the coherence between n adjacent spots, as the spots are created by light having different frequencies, which inherently cannot interfere. Even in embodiments of the system 84 in which the delay paths of the beamlets 92, 94, 96 are equalized, and the n different spots are not actually separated in time, the effective scan rate is still $R_{eff}=Rn$. An advantage of simultaneous temporal and frequency dispersion is the ability to replicate a frequency-dispersed beamlet set at different temporal delays in order to increase the length of a scan line, and thereby increase scanning throughput.

In applications in which an imaging detector is used as the detector unit 98, any needed compensation for different illumination intensities of the returning beamlets 92, 94, 96 can be achieved by incorporating attenuators (not shown) in the detector unit 98.

Third Embodiment

Figure 5:
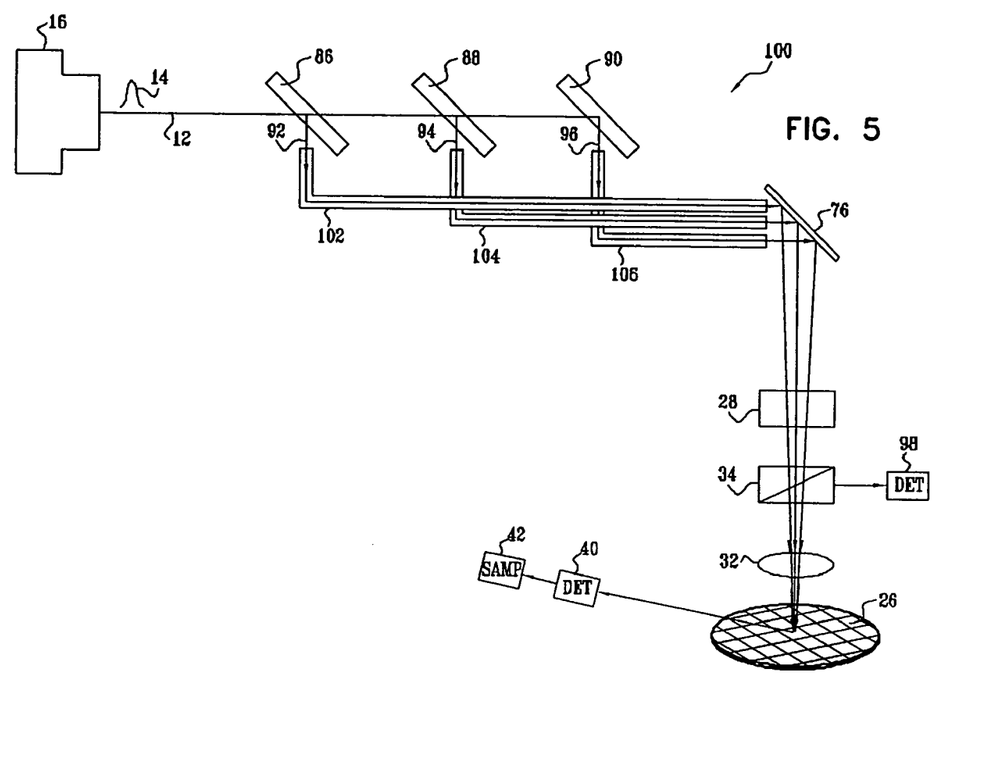
FIG. 5 is a schematic illustration of an optical inspection system, which is constructed and operative in accordance with an alternate embodiment of the invention.

Reference is now made to FIG. 5, which is a schematic illustration of an optical inspection system 100, which is constructed and operative in accordance with an alternate embodiment of the invention. The system 100 is similar to the system 84 (FIG. 4). However, different time delays for the beamlets 92, 94, 96 are now achieved by transmitting the beamlets 92, 94, 96 respectively through optical fibers 102, 104, 106, each fiber having a different length. Thus, the optical paths followed by the beamlets 92, 94, 96 have unique lengths.

Fourth Embodiment

Figures 6, 7:
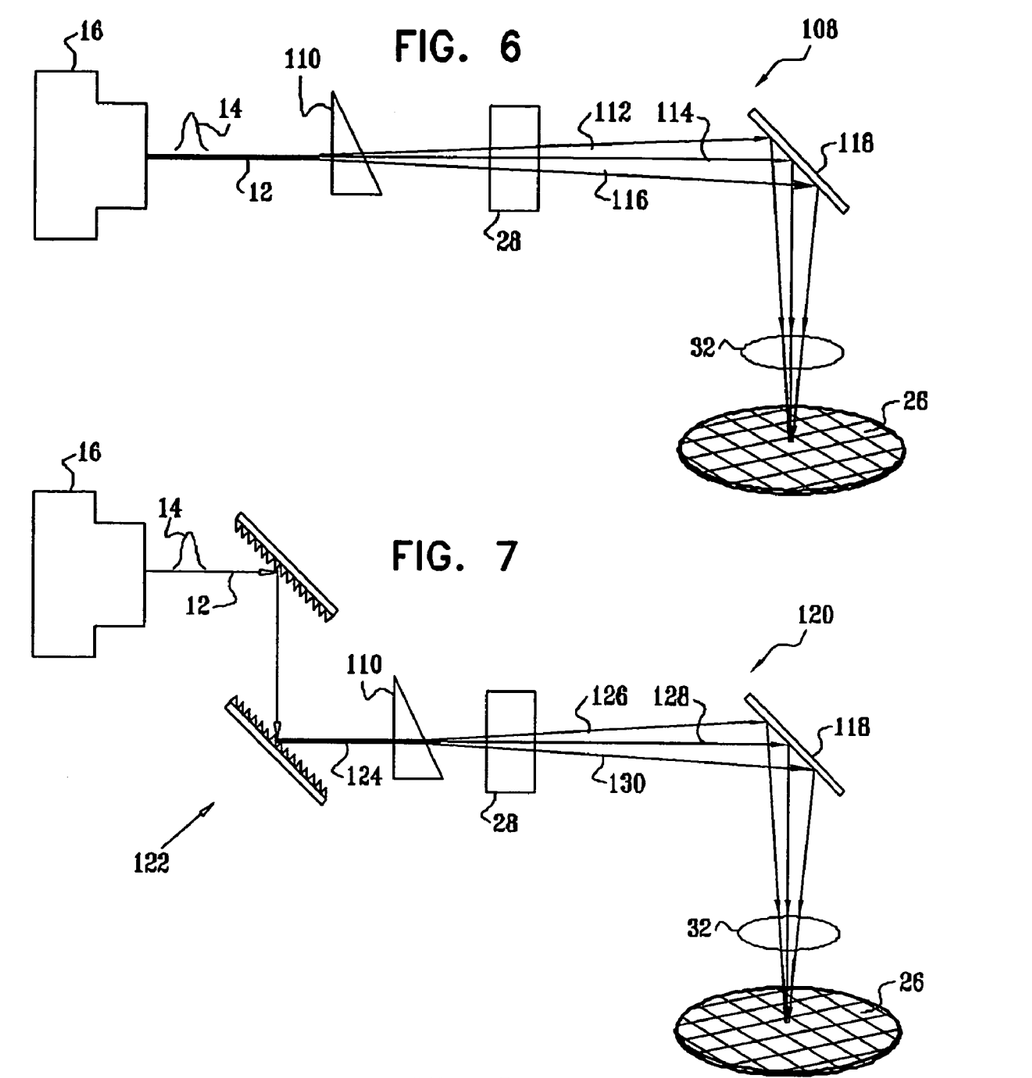
FIG. 6 is a schematic illustration of an optical inspection system employing multiple pulsed beamlets that are spatially dispersed according to waveband, which is constructed and operative in accordance with an alternate embodiment of the invention.
FIG. 7 is a schematic illustration of an optical inspection system employing multiple pulsed spatially separated beamlets, dispersed temporally and by waveband, which is constructed and operative in accordance with an alternate embodiment of the invention.

Reference is now made to FIG. 6, which is a schematic illustration of an optical inspection system 108, which is constructed and operative in accordance with an alternate embodiment of the invention. The description of FIG. 6 should be read in conjunction with FIG. 3.

The beam 12 passes through a prism 110, where it is dispersed spatially according to frequency to form beamlets 112, 114, 116, each having a unique waveband. The prism 110 thus acts as a wavelength manipulator for the beam 12.

The beamlets 112, 114, 116 are scanned by the scanner 28 and are redirected by a reflector 118 through the focusing optics 32 to impinge obliquely or normally on the surface of the substrate 26. Returned light can be detected in the same manner as disclosed in the discussion of the embodiment of FIG. 4, detection components being omitted in FIG. 6 for clarity. The embodiment of FIG. 6 has the advantage of structural simplicity, but is unable to achieve temporal separation of individual illumination spots. It should also be noted that while discrete beamlets are shown in FIG. 6 for clarity, the prism 110 actually creates a continuum of illuminated spots, each of which corresponds to the full numerical aperture of the transmission optics.

Fifth Embodiment

Reference is now made to FIG. 7, which is a schematic illustration of an optical inspection system 120, which is constructed and operative in accordance with an alternate embodiment of the invention. The description of FIG. 7 should be read in conjunction with FIG. 6.

The system 120 is similar to the system 108 (FIG. 6), except that a parallel grating pair 122 is now introduced into the path of the beam 12. The grating pair 122 stretches the pulse 14, and is configured by choosing the distance between the pair, the incidence angle of the beam 12, and the grating period in a known manner, so as to spread the pulse across the entire period between successive pulses emitted by the laser source 16 to produce a frequency-chirped beam 124. The beam 124 transits the prism 110, which separates it into angularly scanned beamlets 126, 128, 130, each having a unique waveband and a unique time delay. In this embodiment, the grating pair 122 and the prism 110 together constitute a beam converter or manipulator, manipulating the beamlets 126, 128, 130 both by wavelength and by time delay.

Figure 8:
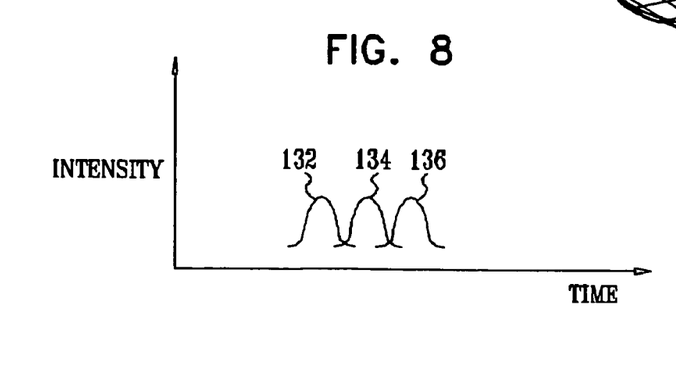
FIG. 8 is a plot of optical activity in the system shown in FIG. 7, illustrating temporal dispersion of beamlets.

Reference is now made to FIG. 8, which is a composite plot illustrating temporal dispersion of the beamlets 126, 128, 130 (FIG. 7). Peaks 132, 134, 136 correspond to the beamlets 126, 128, 130, respectively. Each peak has a different frequency, and is delayed differently from the others. In the system 120, the prism 110 produces a frequency chirped spectral continuum, in which each point of the spectrum has a unique time delay. Discretized representations of the beamlets 126, 128, 130 (FIG. 7), and the peaks 132, 134, 136 are provided for clarity of illustration.

Detection arrangements for the system 120 are disclosed hereinbelow. The spatio-temporal dispersion produced in the system 120 is particularly suited to the use of a single fast non-imaging detector, which can follow the temporal scan. It is also possible to use an imaging array sensor, with appropriate compensation for the spectral intensity distribution.

Referring again to FIG. 7, in the system 120 the scan rate in the direction orthogonal to the primary scan direction can be extremely high, with the total effective scan rate limited only by the modelocked pulse repetition rate. In practice, the pulse repetition rate can be as high as 1 GHz, enabling a scan rate of tens or hundreds of gigapixels per second, depending on the spectral bandwidth. The effective cross-scan rate for n spots is R=n/T, provided that the chirp is sufficient to spread the pulse 14 across the entire period between successive pulses of the laser source 16. The total effective scan rate is $R_{eff}$=Rn.

Sixth Embodiment

Figure 9:
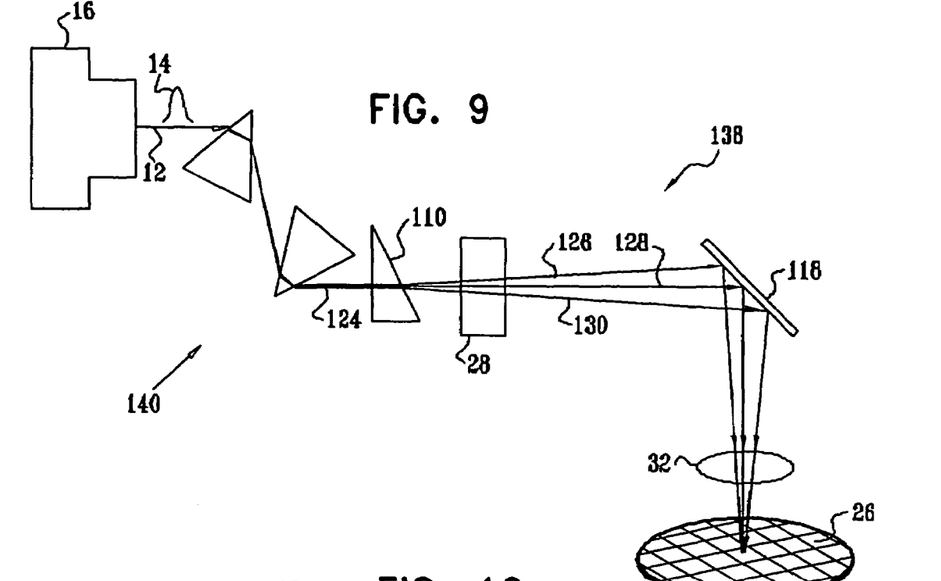
FIG. 9 is a schematic illustration of an optical inspection system employing multiple pulsed spatially separated beamlets, dispersed temporally and by waveband, which is constructed and operative in accordance with an alternate embodiment of the invention.

Reference is now made to FIG. 9, which is a schematic illustration of an optical inspection system 138, which is constructed and operative in accordance with an alternate embodiment of the invention. The description of FIG. 9 should be read in conjunction with FIG. 7.

The system 138 is similar to the system 120 (FIG. 7), except that the grating pair 122 is replaced by a prism pair 140. The prism pair 140 produces a group delay dispersion of the beam 12 to form the beam 124. As in the embodiment of FIG. 7, the pulses of the beam 124 are broadened when compared to the pulse 14, and they display a frequency sweep. The refractive index for the dispersive glass in the prism pair 140 affects the chirp, and is chosen according to the spectrum of the pulse 14, and the time between successive pulses. In this embodiment, the prism pair 140 and the prism 110 together constitute a beam converter, manipulating the beamlets 126, 128, 130 both by wavelength and by time.

Detection.

Figure 10:
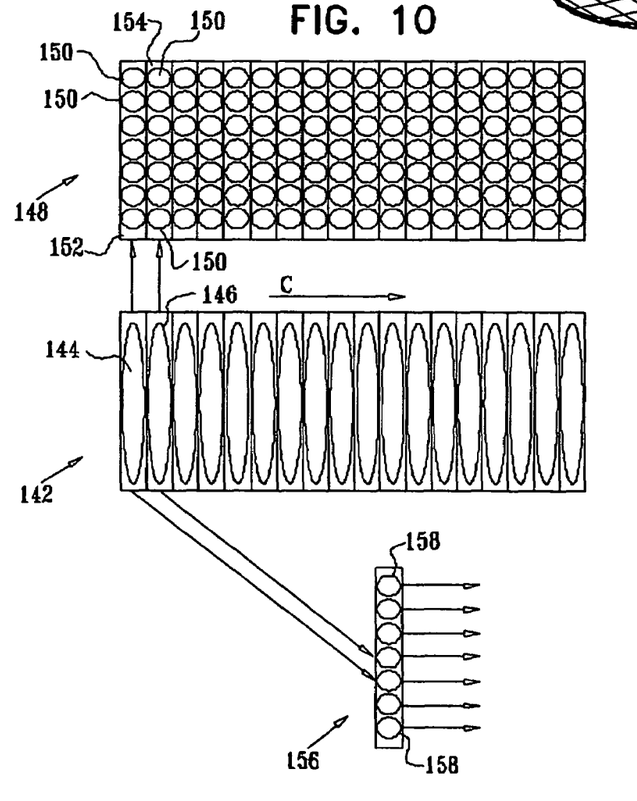
FIG. 10 is a composite schematic representation of detector arrangements, which are used in various embodiments of the invention.

Reference is now made to FIG. 10, which is a composite schematic representation of detector arrangements that are suitable for use in the embodiments disclosed hereinabove. A strip 142 of the substrate is scanned in a primary scanning direction indicated by an arrow C. The scan comprises a plurality of linear areas of illumination, each consisting of a plurality of overlapping spots as disclosed hereinabove. The linear areas are indicated representatively by areas 144, 146. High-resolution bright-field detection, in which the signal-to-noise ratio is very high, may be performed with a known imaging detector 148, e.g., a CCD camera, which collects the light with a long integration time. Each spot is collected to a different detector element or group of detector elements 150 in the imaging detector. Thus, as the scan proceeds, light returning from the area 144 is collected on the detector elements 150 located in a region 152 of the detector 148.

Then light returning from the area 146 is collected on the detector elements 150 located in a region 154.

Alternatively, bright-field detection can be accomplished using a linear detector array 156 having simultaneous parallel readout of detector elements 158, arranged along the secondary scanning direction. As the scan proceeds, light returning from the area 144 is collected on the detector elements 158, which are then read out simultaneously. Next, while the scanner is positioned over the area 146, returning light is again collected on the detector elements 158, and readout is repeated. The process continues until the strip 142 has been fully scanned. Using this arrangement, the collection optics and detector are thus imaging in the secondary scanning direction, but non-imaging in the primary scan direction. Each of the spots illuminated by the individual beamlets, e.g., beamlets 92, 94, 96 (FIG. 4), is imaged to a separate one of the detector elements 158 or to an overlapping group of the detector elements 158, while the collected beam remains essentially stationary on the linear detector array 156. This can be achieved using cylindrical lenses in the collection optics. Unlike a CCD device, which uses a serial readout, the linear detector array 156 should provide parallel readout of all the elements in order to maintain synchronization with the scan. An example of such a linear detector array is the Hamamatsu model S5668, which has a parallel read out of 16 linear elements.

When using an imaging detector, it is important that the collection NA equal the illumination NA in order to avoid undesirable coherence effects.

Alternatively, in embodiments employing temporal dispersion, such as the embodiment of FIG. 3, bright-field detection of a series of adjacent spots may be performed using a very fast single-element non-imaging detector. This is practical, since each spot on the substrate is illuminated in its own time slot. The relationship between the NA of the non-imaging detector and the NA of the illuminator is application dependent. It is acceptable, but not essential for the NA of the collection optics to exceed the NA of the illumination optics. In some cases, it is actually advantageous for the NA of the collection optics to be smaller than the NA of the illumination optics.

Alternatively, in the disclosed embodiments employing spatial wavelength dispersion, such as the embodiment of FIG. 6, bright-field detection of a series of adjacent spots may be performed using a plurality of detectors, each of which is sensitive to a different waveband. The discussion of the relationship between the NA of the illumination optics and the NA of the collection optics for imaging and non-imaging detectors in embodiments employing temporal dispersion is applicable to embodiments employing wavelength dispersion.

In some embodiments of the detection subsystems disclosed hereinbelow, high-NA bright field detectors are cooperative with simultaneously operating low-resolution dark-field detectors. However, it will be appreciated that these embodiments can be readily modified by the application of ordinary skill in the art to provide high-resolution dark field detection capability by replicating the bright field detector apparatus, appropriately disposing the collection optics so as to collect scattered light.

Figure 11:
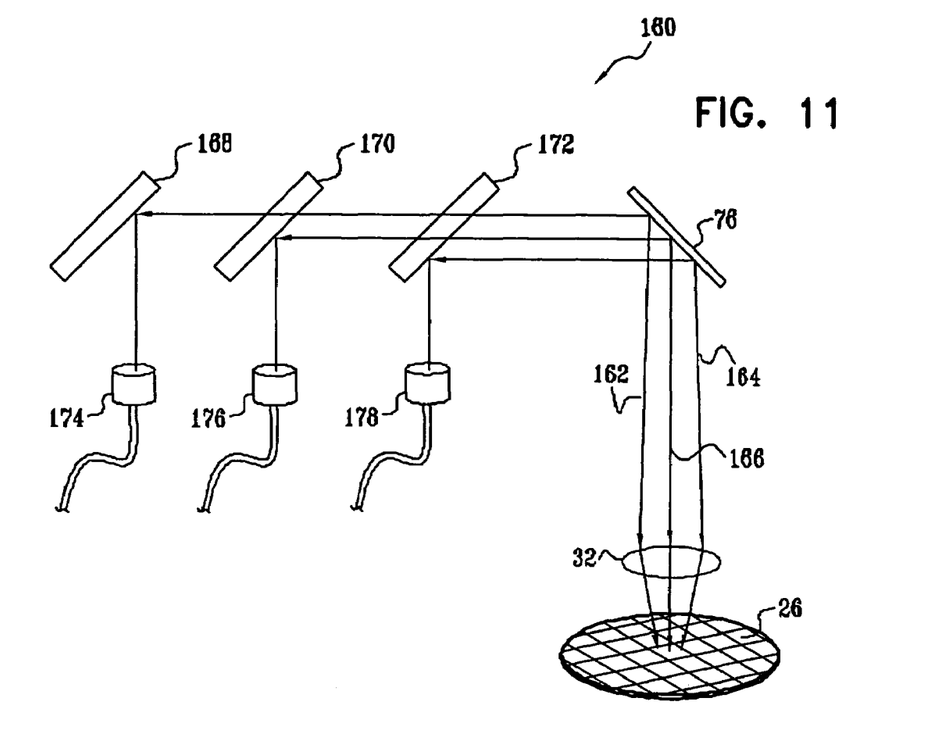
FIG. 11 is a schematic illustration of a detection subsystem for use in optical inspection systems according to various embodiments of the invention.

Reference is now made to FIG. 11, which is a schematic illustration of a detection subsystem 160 for an optical inspection system employing spatial wavelength dispersion, which is constructed and operative in accordance with an alternate embodiment of the invention. A plurality of pulsed beamlets 162, 164, 166, each having a different waveband, are directed by focusing optics 32 onto adjacent spots of the substrate 26. The beamlets 162, 164, 166 can be normal to the substrate 26, or can be obliquely incident thereon. The beamlets 162, 164, 166 may be created by any of the embodiments disclosed hereinabove that employ spatial dispersion according to wavelength, the details of the illuminator being omitted in FIG. 11 for clarity.

Reflected light corresponding to the beamlets 162, 164, 166 returns to the reflector 118. In FIG. 11, the focusing optics 32 function as collection optics for the returned light. Alternatively, a different system of collection optics (not shown) may be provided. The beamlets 162, 164, 166 continue through a series of optical elements 168, 170, 172, which sort the beamlets 162, 164, 166 in order of their respective wavebands. The elements 168, 170, 172 can be reflective edge filters. Returning light from each of the beamlets 162, 164, 166, now isolated by waveband, is received by a respective member of a set of detectors 174, 176, 178, each of which is sensitive to the waveband of its associated beamlet. The detectors 174, 176, 178 can operate at a slower rate than the single-element detector disclosed above, which is used when time dispersion of beamlets is employed.

Figure 12:
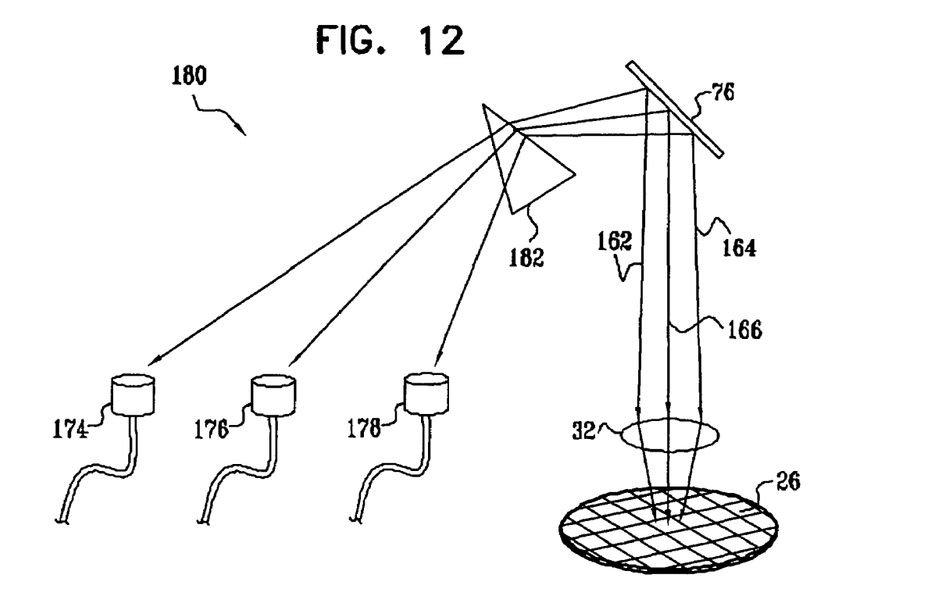
FIG. 12 is a schematic illustration of an alternate detection subsystem for use in optical inspection systems for use in optical inspection systems according to various embodiments of the invention.

Reference is now made to FIG. 12, which is a schematic illustration of a detection subsystem 180 for an optical inspection system employing spatial wavelength dispersion, which is constructed and operative in accordance with an alternate embodiment of the invention. The subsystem 180 is similar to the subsystem 160 (FIG. 11), except that wavelength separation of the beamlets 162, 164, 166 is performed by a prism 182. One or more diffraction gratings may be substituted for the prism 182.

In all the detection schemes disclosed herein, low-NA dark field detection may be additionally performed by simultaneously collecting the light scattered from the multiple illuminated spots.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus for optical inspection, comprising a beam manipulator for converting a pulsed beam into a plurality of spatially separated beamlets incident on a substrate to be inspected, wherein:

said beam manipulator comprises a temporal beam converter;

at least some of said beamlets are directed towards different spots on said substrate;

centers of at least two of said different spots are spaced apart by no more than about 3 spot diameters;

there is substantially no mutual interference among said beamlets, and said temporal beam converter comprises a plurality of beamsplitters and a plurality of retroreflectors, wherein a light path of each of said beamlets extends through at least one of said beamsplitters and through one of said retroreflectors.

2. An apparatus for optical inspection, comprising a beam manipulator for converting a pulsed beam into a plurality of spatially separated beamlets that are incident on a substrate to be inspected, wherein:

said beam manipulator comprises a temporal beam converter;

at least some of said beamlets are directed towards different spots on said substrate;

centers of at least two of said different spots are spaced apart by no more than about 3 spot diameters;

wherein there is substantially no mutual interference among said beamlets, and said temporal beam converter comprises a plurality of optical fibers having different lengths, wherein a light path of each of said beamlets extends through a corresponding one of said fibers.

3. An apparatus for optical inspection, comprising:

a coherent light source producing a pulsed beam, and a beam manipulator for converting said pulsed beam into a plurality of spatially separated beamlets incident on a substrate to be inspected, wherein:

said beam manipulator comprises a temporal beam converter;

said temporal beam converter comprises a plurality of beamsplitters and a plurality of retroreflectors, wherein a light path of each of said beamlets extends through at least one of said beamsplitters and through one of said retroreflectors;

at least some of said beamlets are directed towards different spots on said substrate, and there is substantially no mutual interference among said beamlets; said apparatus further comprising:

a scanner for displacing said beamlets across said substrate, and at least one detector positioned to detect at least two of said beamlets reflected from said substrate.

4. An apparatus for optical inspection, comprising:

a coherent light source producing a pulsed beam, and a beam manipulator for converting said pulsed beam into a plurality of spatially separated beamlets that are incident on a substrate to be inspected, wherein:

said beam manipulator comprises a temporal beam converter;

said temporal beam converter comprises a plurality of optical fibers having different lengths, wherein a light path of each of said beamlets extends through a corresponding one of said fibers;

at least some of said beamlets are directed towards different spots on said substrate, and there is substantially no mutual interference among said beamlets; said apparatus further comprising:

a scanner for displacing said beamlets across said substrate, and at least one detector positioned to detect at least two of said beamlets reflected from said substrate.

* * * * *